US00PP36588P3

(12) United States Plant Patent
Pressler

(10) Patent No.: US PP36,588 P3
(45) Date of Patent: Apr. 8, 2025

(54) MANDARIN TREE NAMED 'AC4916'

(50) Latin Name: *Citrus reticulata*
Varietal Denomination: AC4916

(71) Applicant: C&B Pressler Family Trust, Bundaberg (AU)

(72) Inventor: Craig Robert Pressler, Bundaberg (AU)

(73) Assignee: C&B Pressler Family Trust, Bundaberg (AU)

( * ) Notice: Subject to any disclaimer, the term of this patent is extended or adjusted under 35 U.S.C. 154(b) by 0 days.

(21) Appl. No.: 18/771,592

(22) Filed: Jul. 12, 2024

(65) Prior Publication Data

US 2025/0031589 P1 Jan. 23, 2025

Related U.S. Application Data

(60) Provisional application No. 63/514,075, filed on Jul. 17, 2023.

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202
CPC ..... A01H 6/785; A01H 5/08
See application file for complete search history.

*Primary Examiner* — Keith O. Robinson
(74) *Attorney, Agent, or Firm* — Michelle Bos Legal LLC

(57) ABSTRACT

A new mandarin tree named 'AC4916' notable for its flavorful seedless fruit.

6 Drawing Sheets

Latin name: *Citrus reticulata.*
Common name: Mandarin.
Variety denomination: 'AC4916'.

BACKGROUND AND SUMMARY OF THE VARIETY

'AC4916' is a new mandarin tree that originated as an induced mutation of 'W Murcott' mandarin (not patented) at Queensland, Australia in 2009. Bud sticks of 'W. Murcott' (not patented) were irradiated in 2009, and subsequently grafted onto 'Carrizo' rootstock (not patented) at Queensland, Australia in 2009. 'AC4916' was selected from among the grafted plants for further observation because of its flavorful seedless fruit. The 'AC4916' mandarin tree has been observed to remain true to type over successive asexually propagated generations.

The 'AC4916' mandarin tree is distinguished from 'W. Murcott' as set forth in Table 1 below.

TABLE 1

Comparison of 'AC4916' to 'W. Murcott'

| | 'AC4916' | 'W. Murcott' |
|---|---|---|
| Seeds | Absent | Present |
| Rind thickness | 3.0 mm | 3.8 mm |
| Leaf upper surface color | Yellow-green 147A | Yellow-green 146A |
| Leaf shape in cross-section | Weakly concave, 120° | Strongly concave, 60° |

The 'AC4916' mandarin tree is distinguished from similar variety 'Tango' (U.S. Plant Pat. No. 17,863) as set forth in Table 2 below.

TABLE 2

Comparison of 'AC4916' Mandarin to 'Tango' Mandarin

| | 'AC4916' | 'Tango' |
|---|---|---|
| Growth habit | Spreading | Upright |
| Vigor | Strong | Strong to very strong |
| Fruit rind color | Orange N25B | Orange 24A |
| Fruit length | 60.5 mm | 54.7 mm |

BRIEF DESCRIPTION OF THE PHOTOGRAPHS

The accompanying photographs, which show fifth- and sixthleaf 'AC4916' mandarin trees grown on 'Carrizo' rootstock, were taken in 2023 and 2024 at Visalia, California. The trees were planted in 2019. The colors of the claimed plant and its fruit may vary with lighting conditions. Therefore, color characteristics should be determined with reference to the observations described herein, rather than from these illustrations alone.

Figure 1:
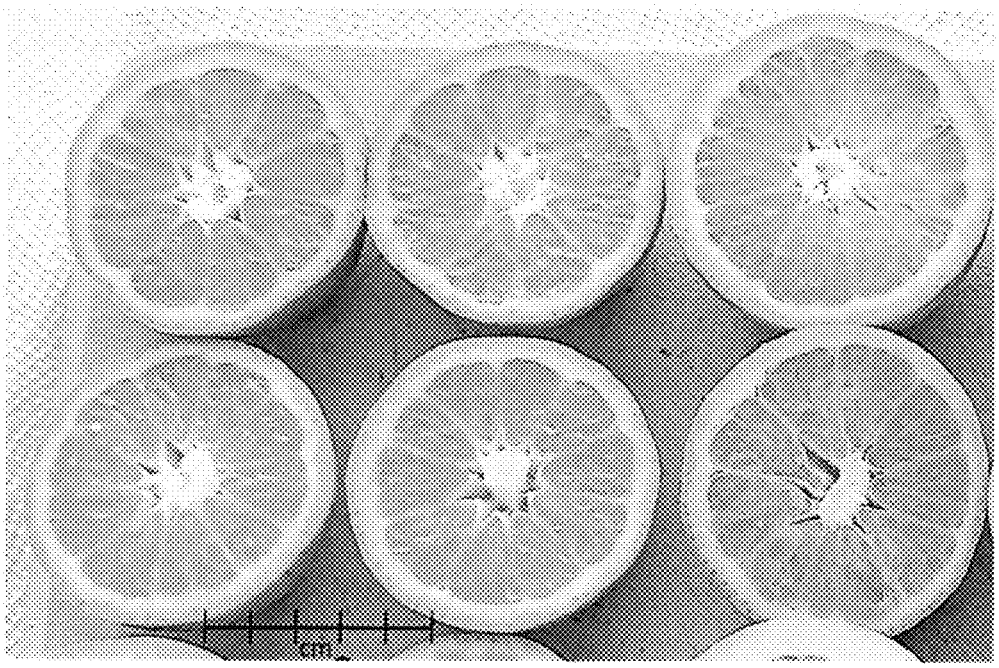
Figure 2:
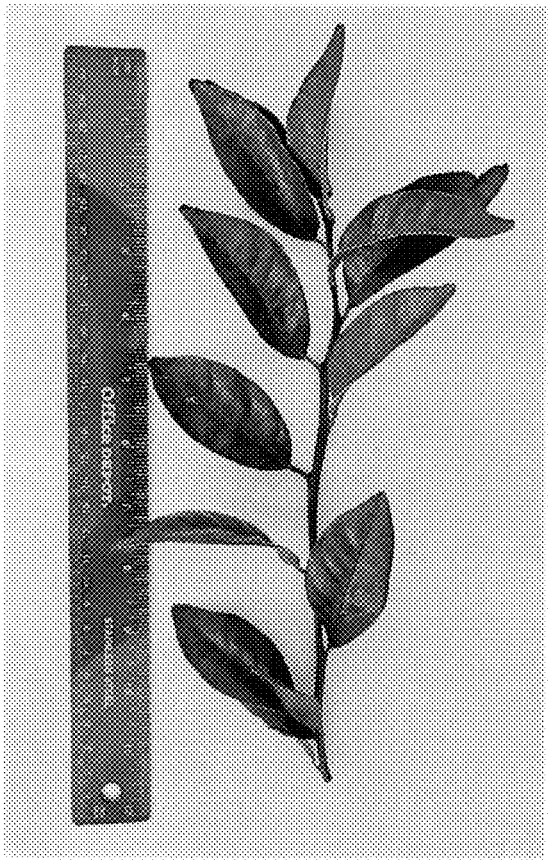
Figure 3:
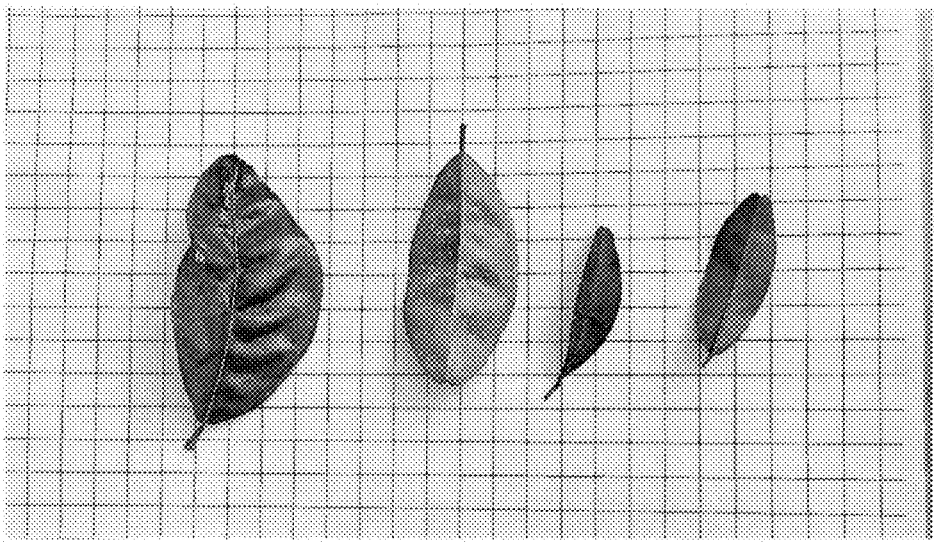
Figure 4:
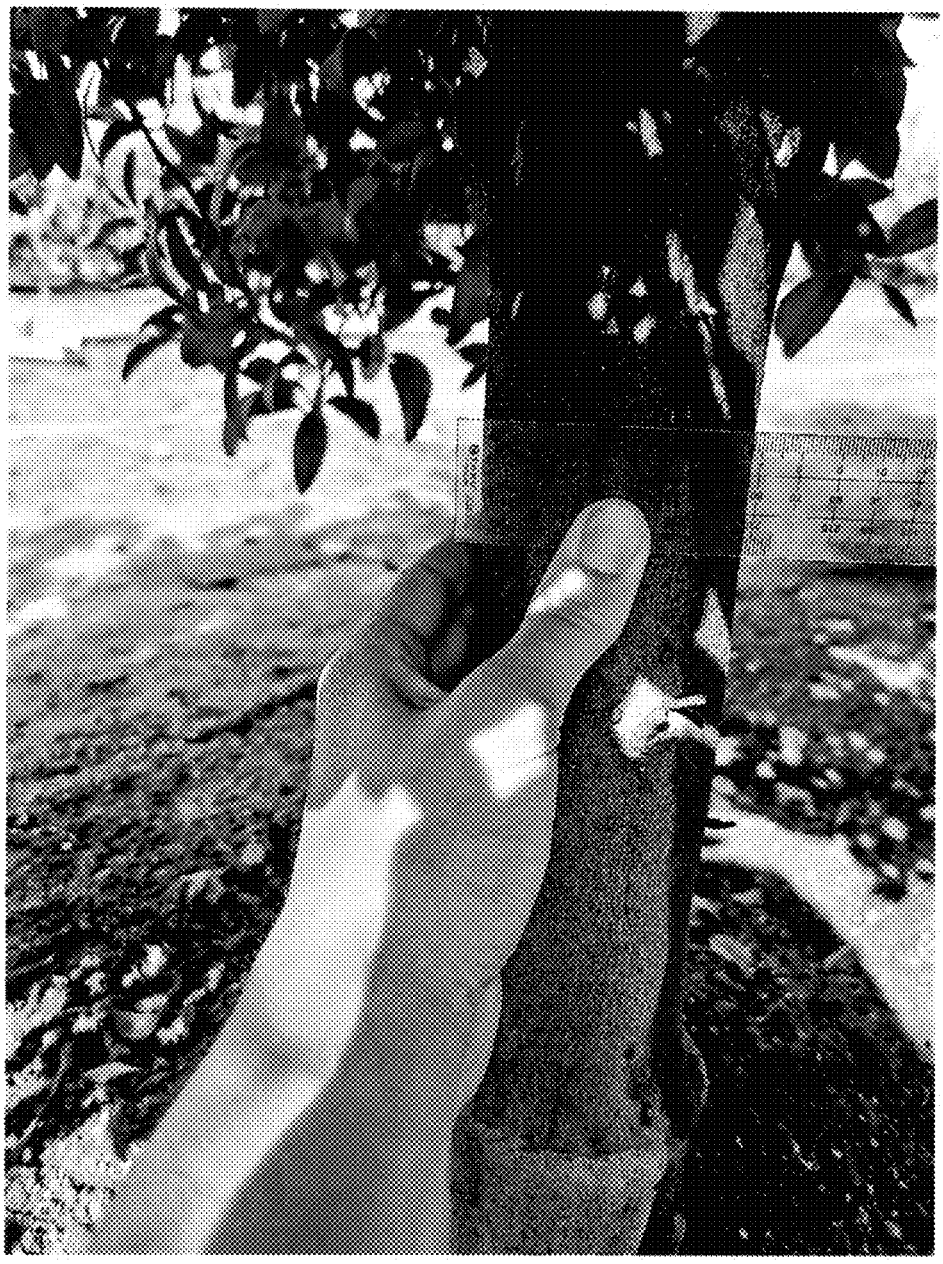
Figure 5:
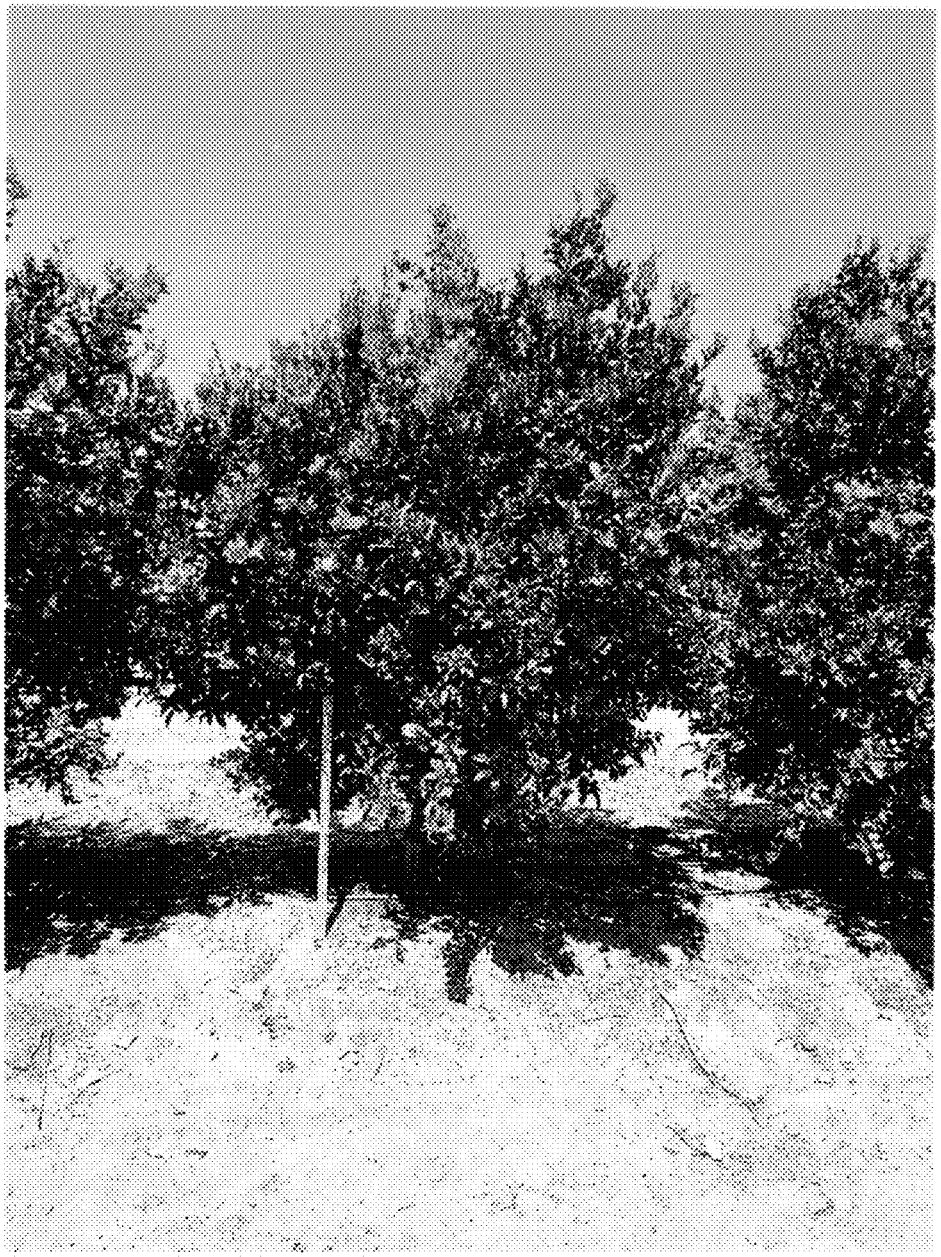
Figure 6:
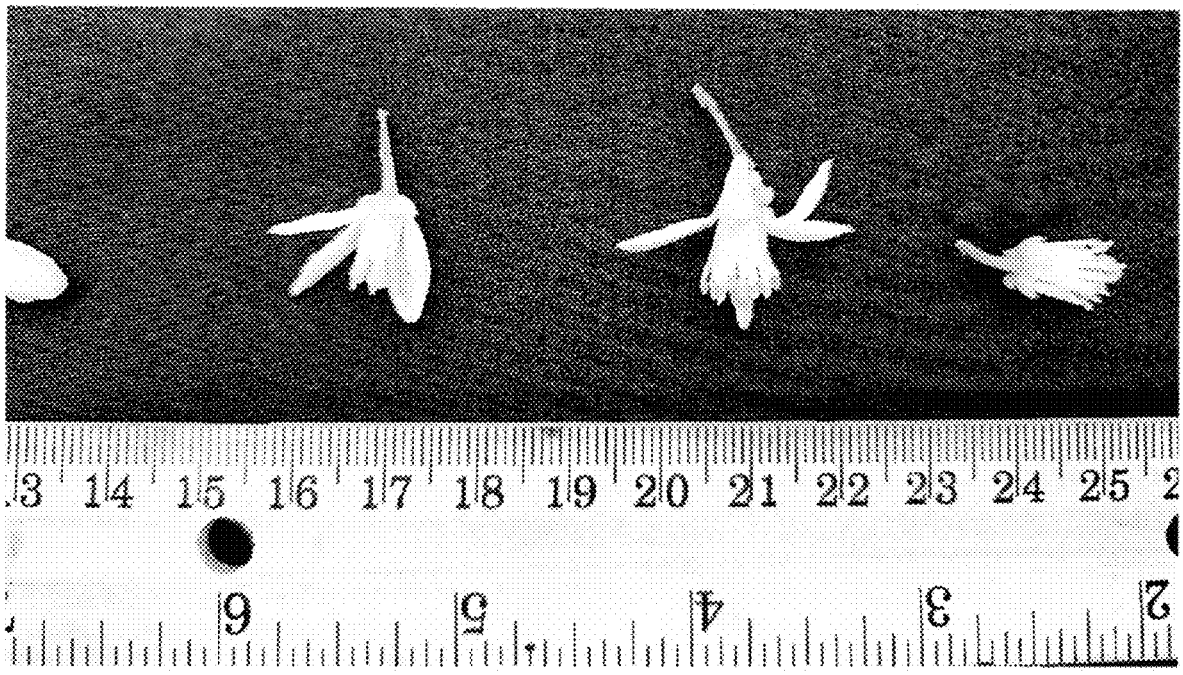

FIG. 1 shows sectioned fruit from an 'AC4916' mandarin tree;
FIG. 2 shows a shoot from an 'AC4916' mandarin tree;
FIG. 3 shows leaves from an 'AC4916' mandarin tree;
FIG. 4 shows the trunk of an 'AC4916' mandarin tree;
FIG. 5 shows an 'AC4916' mandarin tree; and,
FIG. 6 shows flowers of an 'AC4916' mandarin tree.

DETAILED BOTANICAL DESCRIPTION

The following detailed botanical description is based on observations recorded at Visalia, California in 2023 of fifth-leaf trees planted in 2019 on 'Carrizo' rootstock. The characteristics described will vary somewhat depending upon cultural practices, climatic conditions, location and growing season. Quantified measurements are expressed as an average of measurements taken from a number of individual plants of the claimed variety. The measurements of any individual plant or any group of plants of the variety may vary from the stated average. Colors are described with reference to The R.H.S. Colour Chart, 6th edition (Royal Horticultural Society 2019).

DETAILED BOTANICAL DESCRIPTION

Tree:
- *Vigor*.—Medium strong.
- *Density of canopy*.—Medium dense.
- *Habit*.—Spreading.
- *Height*.—3 m.
- *Trunk diameter* (*at* 30 *cm above the graft*).—7 cm to 10 cm.
- *Bark texture*.—Slightly rough.
- *Bark color*.—Grey-brown 199B.

Branch (fruiting branches about 1 m above graft):
- *Length*.—About 1.5 m.
- *Diameter*.—2 cm to 3 cm.
- *Crotch angle*.—Acute.
- *Bark color*.—Grey-brown 199B.
- *Bark texture*.—Slightly rough.
- *Thorns*.—Absent.
- *Current year shoot length*.—70 cm to 72 cm.
- *Current year shoot color*.—Green NN137B.

Flower buds:
- *Shape*.—Oval.
- *Length*.—0.9 cm.
- *Diameter*.—0.5 cm.
- *Bud color*.—White NN155D.

Flowers:
- *Date of first bloom*.—Mar. 27, 2024.
- *Number of flowers per cluster*.—1 to 4.
- *Number of petals per flower*.—5.
- *Flower diameter*.—2.8 cm.
- *Flower depth*.—1.1 cm.

Petals:
- *Shape*.—Strap.
- *Apex*.—Rounded.
- *Margin*.—Entire.
- *Length*.—1.3 cm.
- *Width*.—0.3 cm.
- *Color—upper surface*.—White 155D.
- *Color—lower surface*.—155B.
- *Relative position of petal margins*.—Overlapping.

Pistil:
- *Quantity per flower*.—1.
- *Length*.—7.4 mm.

Stigma:
- *Length*.—1 mm.
- *Stigma color*.—Yellow 13C.

Style:
- *Length*.—4.6 mm.
- *Color*.—Yellow-green 151D.

Ovary:
- *Length*.—2 mm.
- *Diameter*.—2.4 mm.
- *Color*.—Yellow-green 145A.

Stamens:
- *Quantity per flower*.—20.
- *Anther length*.—2 mm.
- *Anther color*.—Yellow-orange 14A.
- *Pollen*.—Present in moderate amount.

Pedicel:
- *Length*.—4 mm.
- *Diameter*.—1 mm.
- *Color*.—Yellow-green N144D.

Sepals:
- *Length*.—2 mm.
- *Sepal width*.—2 mm.
- *Sepal shape*.—Deltoid with acuminate apex.
- *Sepal margin*.—Entire.
- *Sepal color—upper surface*.—Yellow-green 154C.
- *Sepal color—lower surface*.—Yellow-green 154B.

Leaves:
- *Length*.—65 mm to 80 mm.
- *Width*.—35 mm to 45 mm.
- *Length/width ratio*.—1.4 to 2.3.
- *Blade margin*.—Broadly crenate.
- *Leaf shape*.—Broadly elliptic.
- *Apex shape*.—Acute.
- *Base shape*.—Rounded.
- *Texture of upper surface*.—Medium-firm, smooth.
- *Color of upper surface*.—Yellow-green 146A.
- *Color of lower surface*.—Yellow-green 146B.
- *Petiole length*.—6 mm to 10 mm.
- *Petiole diameter*.—1 mm to 2 mm.
- *Petiole color*.—Yellow-green N144A.
- *Wings*.—Absent.

Fruit:
- *Axial diameter*.—74.1 mm.
- *Apical diameter*.—60.5 mm.
- *General shape in profile*.—Oblate.
- *Position of broadest part*.—Middle.
- *Shape in cross-section*.—Round.
- *Presence of neck*.—Absent.
- *Presence of depression at stalk end*.—Present.
- *Presence of areola*.—Absent.
- *Presence of navel*.—Absent.
- *Rind color*.—Orange N25B.
- *Rind thickness*.—3.4 mm.
- *Ease of peeling*.—Easy to medium.
- *Rind texture*.—Smooth to medium.
- *Rind glossiness*.—Strong.
- *Albedo color*.—Yellow 15D.
- *Quantity of fruit segments per fruit*.—9 to 12.
- *Toughness of segment membrane*.—Weak.
- *Juice sac length*.—8 mm to 12 mm.
- *Juice sac shape*.—Elongated.
- *Juice sac color*.—Yellow-orange N21A.
- *Flesh color*.—Orange N25B.
- *Juice soluble solids*.—8.8° Brix.
- *Relative harvest maturity*.—January to May; after 'Tango' (U.S. Plant Pat. No. 17,863), a middle to late maturing variety.
- *Parthenocarpy*.—Present.
- *Seeds*.—None.

Market use: Fresh.

Keeping quality: Excellent.

Shipping quality: Excellent.

I claim:

1. A new and distinct mandarin tree named 'AC4916' substantially as described and illustrated herein.

* * * * *